United States Patent [19]

Nazaryan

[11] Patent Number: 4,940,946
[45] Date of Patent: Jul. 10, 1990

[54] POOL WATER SENSOR WITH AN EXTENDIBLE PRONGED PROBE FOR DETERMINING PH AND CHLORINE LEVELS

[76] Inventor: Sampson Nazaryan, 17955 Arenth Ave., City of Industry, Calif. 91748

[21] Appl. No.: 284,012

[22] Filed: Dec. 13, 1988

[51] Int. Cl.$^5$ .................... G01N 27/416; G01N 27/02
[52] U.S. Cl. ..................................... 324/438; 324/439; 324/156; 324/149
[58] Field of Search ............... 324/438, 439, 444, 446, 324/65 P, 156, 149; 204/1 T, 433; 210/103, 169

[56] References Cited

U.S. PATENT DOCUMENTS

| | | | |
|---|---|---|---|
| 3,942,546 | 3/1976 | Radd et al. | 73/23 |
| 3,956,094 | 5/1976 | Capuano | 324/425 |
| 3,959,087 | 5/1976 | Morrow | 204/18 |
| 4,090,925 | 5/1978 | Jungman | 204/1 T |
| 4,174,500 | 11/1979 | Kuga | 324/115 |
| 4,260,950 | 4/1981 | Hadden | 324/438 |
| 4,550,011 | 11/1985 | McCollum | 324/65 P |
| 4,581,121 | 4/1986 | Dailey et al. | 204/1 B |
| 4,696,189 | 9/1987 | Hochreuther | 324/149 |
| 4,752,360 | 6/1988 | Jasinski | 324/65 C R |
| 4,752,740 | 6/1988 | Steininger | 324/438 |

Primary Examiner—Reinhard J. Eisenzopf
Assistant Examiner—Jack B. Harvey
Attorney, Agent, or Firm—Edwin E. Greigg

[57] ABSTRACT

A hand held sensor body with a manually extendible two-pronged probe contains an ion meter for both chlorine concentration and for pool water acidity. The sensor is D. C. powered and the probe has dual metallic rods extending from the hand-held probe and terminating in alloy sensor tips. The body of the sensor containing the meter also detachably encases the hand-held probe when the probe is not in use. The meter case tapers downwardly in width to a battery chamber with access for the probe cable. The battery chamber has contacts for connection to the meter and an electrical contact for the control knob for an adjustable potentiometer imposed in the electrical circuit between the meter and the probe.

6 Claims, 2 Drawing Sheets

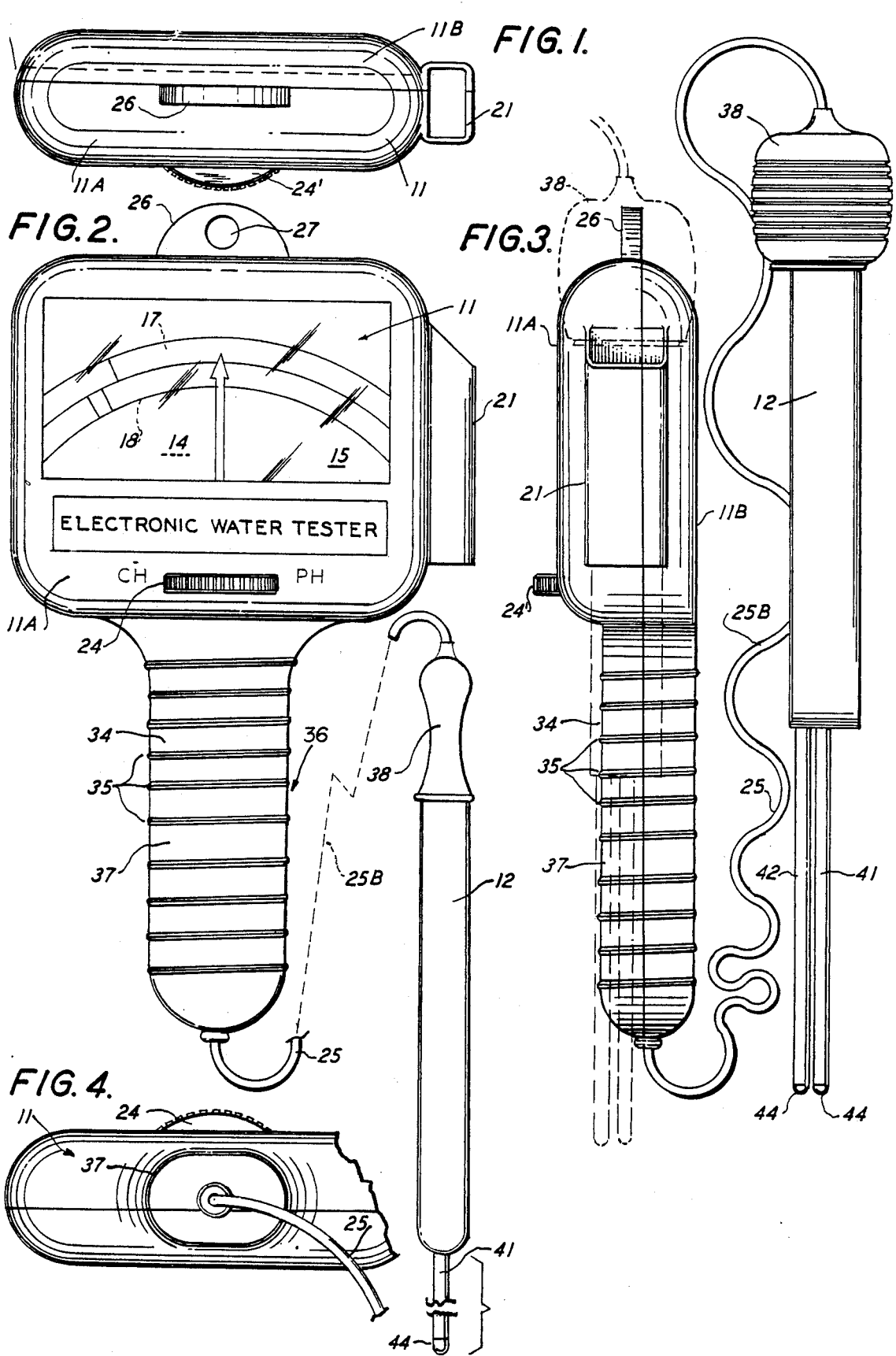

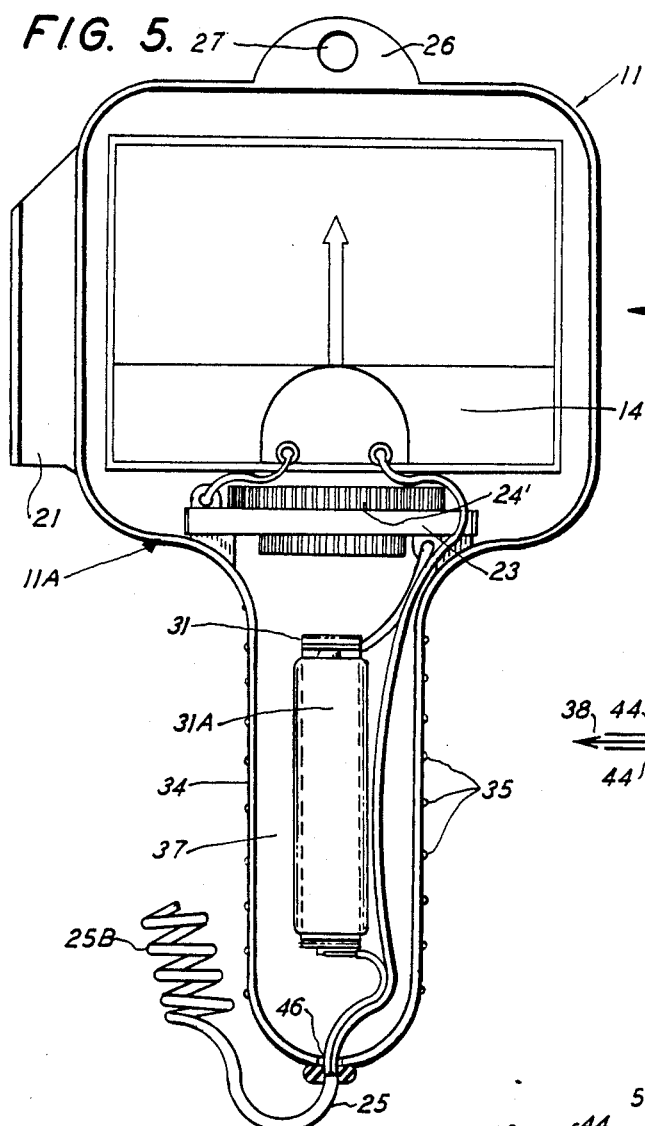
FIG. 5.
FIG. 6.
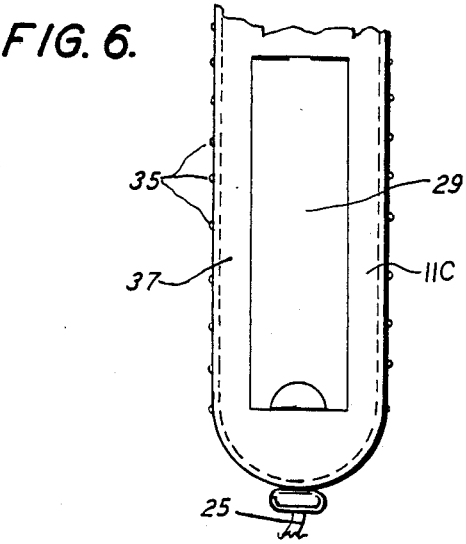
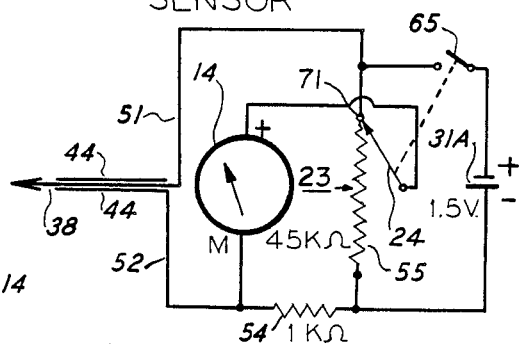
FIG. 7. SENSOR
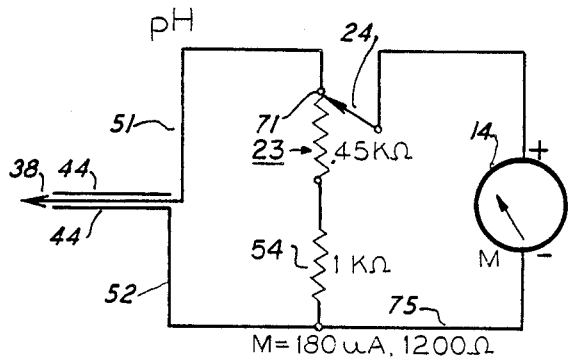
FIG. 8. pH
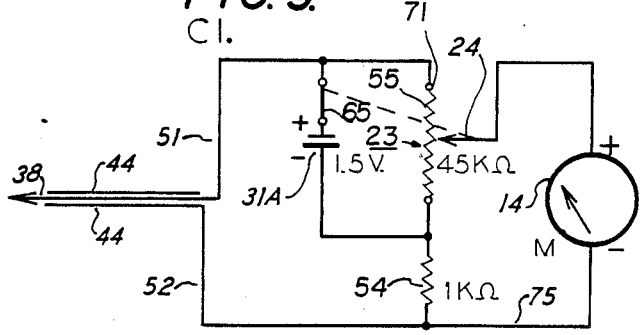
FIG. 9. Cl.

POOL WATER SENSOR WITH AN EXTENDIBLE PRONGED PROBE FOR DETERMINING PH AND CHLORINE LEVELS

RELATED APPLICATION

This application is a continuation of application Ser. No. 06/916,415, filed Oct. 7, 1986, now abandoned.

BACKGROUND OF THE INVENTION

A recurring problem and chore for swimming pool maintenance workers and for pool owners is the task of detecting and correcting the chemical balance of swimming pool water. Large commercial pools may have permanent testing equipment in circulating lines not economically possible for owners of smaller pools like those found in the average household. Acidity must be determined along with chlorine level to insure that pool water is kept free from bacteria and algae and yet safe for human eyes and skin and hair. Accurate small instruments to determine swimming pool water acidity or "Ph", and chlorine concentration are essential to know how much corrective chemical or additive is needed.

I have invented a small, hand-held device of great accuracy and sensitivity that may be carried in one hand to probe for the required concentrations from the edge of the swimming pool.

SUMMARY OF THE INVENTION

The invention contemplates a hand-held sensor for detecting swimming pool water acidity and chlorine concentration and comprises a sensor case, an extendible hand-held probe with dual elements, a probe holster on a side of the case and ion meters within the case. Also contained in the case are meter scales for both functions that are visible from outside the case, a potentiometer to calibrate the meters, a D.C. power source and a flexible electrical cable connecting between the probe and the components within the case.

The case may be plastic and made in two mirror halves joined after assembly with the electrical components and ultra-sonically welded together. The D. C. source may be 1.5 volt battery as used commercially in a great variety of tools, toys and games.

The invention has the advantage of accuracy enhanced by the alloy probe tips and is portable, self-powered for use anywhere. The invention is easy to manufacture, use and store and the power source may be easily replaced as needed.

These and other advantages of the invention are apparent from the following detailed description and drawing.

BRIEF DESCRIPTION OF THE DRAWING

FIG. 1 is a top plan view of the sensor of the invention with the probe thereof removed from the case holster;

FIG. 2 is a front elevational view thereof with the probe shown fragmentarily linked thereto by a broken line electrical cord;

FIG. 3 is a right side elevational view thereof with the probe fully shown and shown in the case holster in broken lines;

FIG. 4 is a fragmentary bottom plan view of the sensor case;

FIG. 5 is a rear elevational view of the sensor case showing the rear case half removed to shown the sensor interior parts;

FIG. 6 is a fragmentary rear elevational view of the sensor case battery holder handle;

FIG. 7 is a combined electrical diagram of the meter testing circuit of the pool water sensor;

FIG. 8 is an electrical diagram of the acidity detecting circuit of the sensor as taken from FIG. 7; and FIG. 9 is an electrical diagram of the chlorine concentration sensor circuit as taken from FIG. 7.

In the drawing like parts are referred to by like characters.

DESCRIPTION OF THE PREFERRED EMBODIMENT

In FIGS. 1 through 6 a swimming pool sensor of pool water condition having a sensor case 11 with front and back molded halves 11A, 11B, is shown with a connected sensor probe 12. Sensor case 11, with its respective halves 11A, 11B, contains a sensing meter 14 (see FIG. 5) behind a transparent face 15 in front side or half 11A of the case, that the operator looks through to read meter scales 17 and 18. The scales show graphically how the meter 14 perceives the acidity, and the chlorine levels, respectively, of the swimming pool water into which the probe unit of the sensor is thrust after the sensor probe is manually extended from a case holster 21 open at top and bottom. The case is preferably molded from plastic in two parts (11A and 11B) that may be joined following assembly with the meter and potentiometer 23 and probe cord 25. Potentiometer adjustment knob 24 is visible in FIGS. 1 through 5.

As can be seen from FIG. 2, a hang tab 26 with an horizontal aperture 27 affords means for hang storage of the sensor where convenient, like near to the swimming pool. Also, a battery door 29 in back half 11B of the sensor case 11 (FIG. 6) provides for access to the battery clip 31 to change batteries when needed. In FIG. 5 it is apparent the blank wall 11C and the battery door each are part of rear half 11B of the sensor case, thus deviating from the mirror image of the front case half. The front half 11A also has a lower panel 34 of parallel horizontal ridges 35 that may be ornamental but serve also as a gripping surface for the user. The ridges are seen in FIGS. 2 and 3, with each ridge adding to grip area 36 that may be impressed at the time sensor case 11 is molded or otherwise formed. Ridges as gripper extend nearly across the width of a battery chamber portion 37 of the sensor case 11.

In FIG. 2 the sensor probe 12 is shown outside of case holster 21 and probe cord 25 can be seen to run from the bottom of battery chamber portion 37 to a coiled section 25B (FIG. 3), with the end of the probe cord entering a probe head 38, within which it contacts two anchored parallel probe elements 41, 42. The probe cord is of two sheathed cables that act as electrical connectors. The parallel elements, preferably of aluminum, normally extend about 125 mm. below the probe head, that is about 50 mm. long, itself. The case holster 21 must therefore be placed on the case to accommodate a probe length of about 175 mm.

Each probe element 41, 42 terminates in a tip 44 (shown in FIGS. 2 and 3) of alloy metal. The alloy is best suited electrically to the meter employed if made from aluminum, lead and silver, with a preponderance of aluminum. Cord 25, being a double strand, is easily connected to the elements within the probe head. With the coiled section providing extension, the operator may reach to immerse the probe elements into the swimming pool water without wetting the sensor case, and observe at close range the sensor readings resulting from the wetted elements. The probe cord 25 enters the sensor probe case by way of an entry port 46 (shown in FIG. 5) formed in each case half when the case is molded, the port being at the middle of the bottom of the battery chamber portion 37.

While the illustrative embodiment shows a 1½ volt battery dry cell in place in the circuit the invention does not preclude a preferable 9 volt cell in the same place-clip 31. Simple alteration of door 29 and battery clip 31 easily accommodate the sensor of the invention to long lasting, readily obtainable 9 volt cells, without diverging from the spirit of the invention. Also, similar modifications may be made in the housing and even meters to accept multiple cells as desired, without appreciably affecting the operation of the pool water sensor.

The sensor, as shown schematically in FIG. 7 is a combined circuit for separately determining acidity and chlorine level in a pool of water. FIG. 7 shows the circuit for determining the acidity and chlorine level meter functions and is comprised of electrical leads 51, 52 from the probe head 38 which connects with one end of a 45K ohm resistor 55 which is the resistor of the potentiometer 23 and to one end of a 1K ohm resistor 54, the other end of resistor 54 connects with the opposite end of resistor 55. Resistor 55 is variable by means of a tap 24 that leads to the positive side of a meter 14 while the negative side of the meter is in parallel with the other resistor 54. Both resistors are in parallel with battery 31A held in battery clip 31. A switch 65 intervenes between the battery and probe lead 51 and is ganged with resistor tap 24 so that when the switch 65 is open, the tap 24 is at the end 71 of resistor 55 as shown in FIGS. 7 and 8. When the switch is closed, the tap is adjustable along the resistor 55 as shown in FIG. 9.

The circuit as seen in FIG. 8 has been carved from the circuit shown in FIG. 7 and is for detecting the acidity or pH level of the pool water into which the sensor probe is placed. FIG. 9 shows schematically a circuit which has been carved from FIG. 7 and is for detecting the chlorine level of the pool water. The acidity sensitivity of the illustrated circuit is variable from between a pH of 1 to pH 9. The chlorine detection is capable of sensing from 0 through 35 PPM, in terms of parts per million of chlorine ions.

In FIG. 8 electrical leads 51, 52 connect respectively, to resistors 55 and 54 with values of values of 45KΩ and 1KΩ, linked in parallel between the probe leads and meter 14. A variable tap 24 on resistor 55 is connected to the positive side of meter 14 and an electrical lead 75 joins resistor 54 to the negative side of meter 14. The circuit as shown reads correctly the electrical flow or conductivity between probe tips 44 in the pool water, for pH.

FIG. 9 similarly shows the circuit for sensing the presence of chlorine ions in the pool water. The circuit includes linkage to battery 31A, placed in parallel between probe lead 51 and the adjacent ends of the resistors 54 and 55. The variable resistor 55 in FIG. 9 has a value of 45KΩ, as is needed with the employed meter to measure electrical flow related to chlorine level in the pool water.

In operation of the device for measuring acidity or PH, the probes 41, 42 are placed in the water and due to the charged ions produced due to the acid, an electrical current is generated which causes the meter to register. The scale of the PH meter has been graduated according to acidity so that when the meter registers a reading which is viewed on the scale, chemicals may be added if necessary to bring the water up to the proper acidity. In measuring for chlorine content, the adjustable knob 24' is rotated toward chlorine as indicated on the housing, FIG. 1, and the probe is inserted into the water. The battery produces current for movement of the meter in accordance with the parts per million of chlorine in the water. Thus, the single meter having two scales and two separate circuits may be used for determining acidity or PH, as well as chlorine.

The invention accomplishes the function of uniquely combining smooth, attractive appearance with the values functionally of easy use, visibility and maintenance, in a package that lends itself to mass production at a cost surprisingly low in view of the accuracy of the measurements obtained. With the ease of a separable probe, an outside indicator and a thumb control use is simplified.

The foregoing description and drawing are to be regarded as illustrative only. Many variations may occur to those skilled in this particular art within the scope of the invention. It is therefore desired that the invention be measured by the attached claims to invention rather than the illustrative material herein.

I claim:

1. A hand-held, portable, self-contained, battery-operated electrical sensor for separately measuring levels of acidity and chlorine concentration of water in a swimming pool which comprises a sensor case, a meter including a pair of meter scales and a meter needle with said sensor case, an on-off electrical switch ganged to a movable tap of a variable control resistor electrical circuit for operating said meter needle, said on-off electrical switch and said variable control resistor being operable together from the case exterior to separately determine acidity and chorine, a sensor probe, a holster adapted to removably hold said sensor probe to said sensor case, said sensor probe including a probe head, spaced apart elongate metallic probe elements extending from said probe head, said elongate metallic probe elements including spaced tips, an extendible flexible electrical cable connecting between said sensor probe elements and said control resistor in the case interior, means for viewing said meter from said case exterior, and a battery chamber within said sensor case, said electrical sensor comprising an electrical circuit with said on-off electrical switch in an open position for separately determining pool water acidity and an electrical circuit with said on-off switch in a closed position for determining water chlorine conditions upon immersion of said sensor probe elements into said water of said swimming pool.

2. A battery operated electrical sensor in accordance with claim 1 wherein the sensor case comprises a meter case portion, a probe holding portion, and a battery holding portion, the probe holding portion being attached to a side of the sensor case and said battery holding portion extending from the meter case portion and reduced in width therefrom.

3. A battery operated electrical sensor in accordance with claim 1 wherein said sensor case is molded in two halves, one half a substantially mirror image of the other half, and said halves are joined together to enclose said meter and said control resistor and said battery chamber.

4. A battery operated electrical sensor in accordance with claim 1, in which said electrical circuit for determining acidity consists of said variable control resistor, said variable control resistor including a resistor and a movable tap (24) movable along said resistor, a second resistor in series with said resistor of said variable control resistor, one side of said meter being connected to said tap and another side of said meter being connected to one end of said second resistor, said meter being electrically in parallel with the series connection of said resistor of said variable control resistor and said second resistor, with one of said sensor probe elements connected to one end of said variable control resistor and one other of said sensor probe elements connected to one end of said second resistor in series with said variable control resistor.

5. A battery operated electrical sensor in accordance with claim 1 in which said electrical circuit for determining chlorine conditions consists of said variable control resistor, said variable control resistor including a resistor and a movable tap (24) movable along said resistor, a second resistor in series with said resistor of said variable control resistor one side of said meter being connected to said tap with an other side of said meter connected with one end of said second resistor in series with said resistor of said variable control resistor, one of said sensor probe elements connected to one end of said resistor of said variable control resistor, one other of said sensor probe elements connected to one end of said second resistor in series with said resistor of said variable control resistor, a battery connected in parallel with said resistor of said variable control resistor and an electrical switch between said battery and said resistor of said variable control resistor, and said electrical switch is ganged to said tap of said variable control resistor.

6. A battery operated electrical sensor in accordance with claim 1, in which said probe elements include spaced tips formed of aluminum, silver and lead.

* * * * *